United States Patent [19]

Storz

[11] Patent Number: 5,112,329
[45] Date of Patent: May 12, 1992

[54] FOUR JOINT MEDICAL INSTRUMENT WITH AN ENDOSCOPE

[76] Inventor: Karl Storz, Auf dem Schildrain 39, 7200 Tuttlingen, Fed. Rep. of Germany

[21] Appl. No.: 566,581

[22] Filed: Aug. 13, 1990

[30] Foreign Application Priority Data

May 1, 1990 [DE] Fed. Rep. of Germany ....... 4000170

[51] Int. Cl.⁵ ............................................. A61B 17/32
[52] U.S. Cl. ...................................................... 606/46
[58] Field of Search ................................ 128/45-50, 128/41

[56] References Cited

U.S. PATENT DOCUMENTS

| 3,901,242 | 8/1975 | Storz | 606/46 |
| 3,973,568 | 8/1976 | Iglesias | 606/46 |
| 4,060,086 | 11/1977 | Storz | 606/46 |

FOREIGN PATENT DOCUMENTS

| 2628555 | 12/1977 | Fed. Rep. of Germany | 606/46 |
| 2915271 | 10/1980 | Fed. Rep. of Germany | 606/46 |

*Primary Examiner*—Max Hindenburg
*Attorney, Agent, or Firm*—William A. Drucker

[57] ABSTRACT

The invention relates to a medical instrument with an endoscope, in which a wire loop, gripping arms or the like are arranged in displaceable manner in the longitudinal direction of the endoscope, as well as with a telescopic periscope which is displaceable together with the wire loop electrode or the like and in which between a ring connected to the telescopic periscope and an axially displaceable slide, which, is connected to the wire loop or the like, are arranged first and second levers interconnected by means of a first joint so that the first lever is connected by means of a second joint to the slide, while the second lever is connected by means of a third joint to the ring, a connection between its end to the periscope and at its other end by a fourth joint being connected between the two joints of the second lever so that the ratio of the spacing of the fourth joint with respect to the first joint is selected so that there is a smaller periscope displacement than wire loop electrode displacement. In order to simplify construction and make handling easier, the invention proposes that the fourth joint of the second lever by arranged on the fixed ring and that the third joint be directly connected to the movable ring.

4 Claims, 3 Drawing Sheets

FOUR JOINT MEDICAL INSTRUMENT WITH AN ENDOSCOPE

BACKGROUND OF THE INVENTION

1. Field of the Invention

The invention relates to a medical instrument with an endoscope to the preamble of claim 1.

2. Brief Description of the Prior Art

An electrosurgical instrument with the above noted features is already known, in which an angular intermediate member is provided between the fixed ring and an elongated hole in the second lever (German patent 26 28 555). Another instrument is known, in which several gripping arms are centrally displaceable in the endoscope shaft and there is also a follow-up of the periscope (European patent 117 894).

In the known instruments of this type, a wire loop carrier, e.g. comprises two parallel tubular rods, which are guided by means of a few guidance parts on the periscope and are interconnected and, at the patient-near end, carry the said wire loop (German utility model 19 41 759). On the working member there is generally provided a straight sliding link mechanism, through which the surgeon can operate the wire loop which is supplied with a radio-frequency current at the patient-near end. Such instruments are used for removing tissue in the urethra and the bladder.

In other constructions, use is made of an endoscopic periscope with a large field of view, which facilitates the operation. However, the endoscope shaft end is always visible in the field of view, which has a disturbing effect.

In addition, a probe is known for the removal of ureteroliths with a gripper arrangement positioned at the front end of a catheter tube and which can be opened and closed by means of an operating cable guided within said tube. On the front end of the catheter tube is arranged a longitudinally displaceable sleeve which carries a radially widenable, inflatable cuff. In addition, an image transmitting light guide is provided concentrically in a ball. In general terms, the image transmission through the flexible light guide is inferior to that with a rigid periscope. Moreover, such a probe cannot be used in certain medical cases, where a rigid endoscope is required (DE-OS 2 927 726).

SUMMARY OF THE INVENTION

The purpose of the invention is to so improve the instrument of the aforementioned type, that the construction is simplified and handling made easier.

According to the invention this problem is solved by providing a medical instrument with an endoscope, in which a wire loop, gripper arms or the like are displaceable in the longitudinal direction of the endoscope and with a telescopic periscope which is displaceable together with the wire loop electrode or the like. First and second levers interconnected by means of a first joint are positioned between a ring connected to the telescopic periscope and an axially displaceable slide which is connected to the wire loop or the like so that the first lever is connected by means of a second joint to the slide, while the second lever is connected by means of a third joint to the ring with a connection between its end toward the periscope and its other end is brought about by a fourth joint between the two joints of the second lever. The ratio of the spacing of the fourth joint with respect to the first joint is selected so that the periscope displacement is smaller than the wire loop electrode displacement, the fourth joint of the second lever being arranged on the fixed ring and the third joint being directly connected to the movable ring. Thus, it is possible to obviate one component of the known instrument, namely the angular intermediate member, which simplifies said instrument. Handling is also made easier because the motion of the sliding link mechanism takes place more easily than hitherto.

BRIEF DESCRIPTION OF THE DRAWINGS

The invention is described in greater detail hereinafter relative to a non-limitative embodiment and with reference to the drawings, wherein:

FIG. 4 is a plan view of only the central part of the embodiment.

DESCRIPTION OF THE PREFERRED EMBODIMENT

Figure 1:
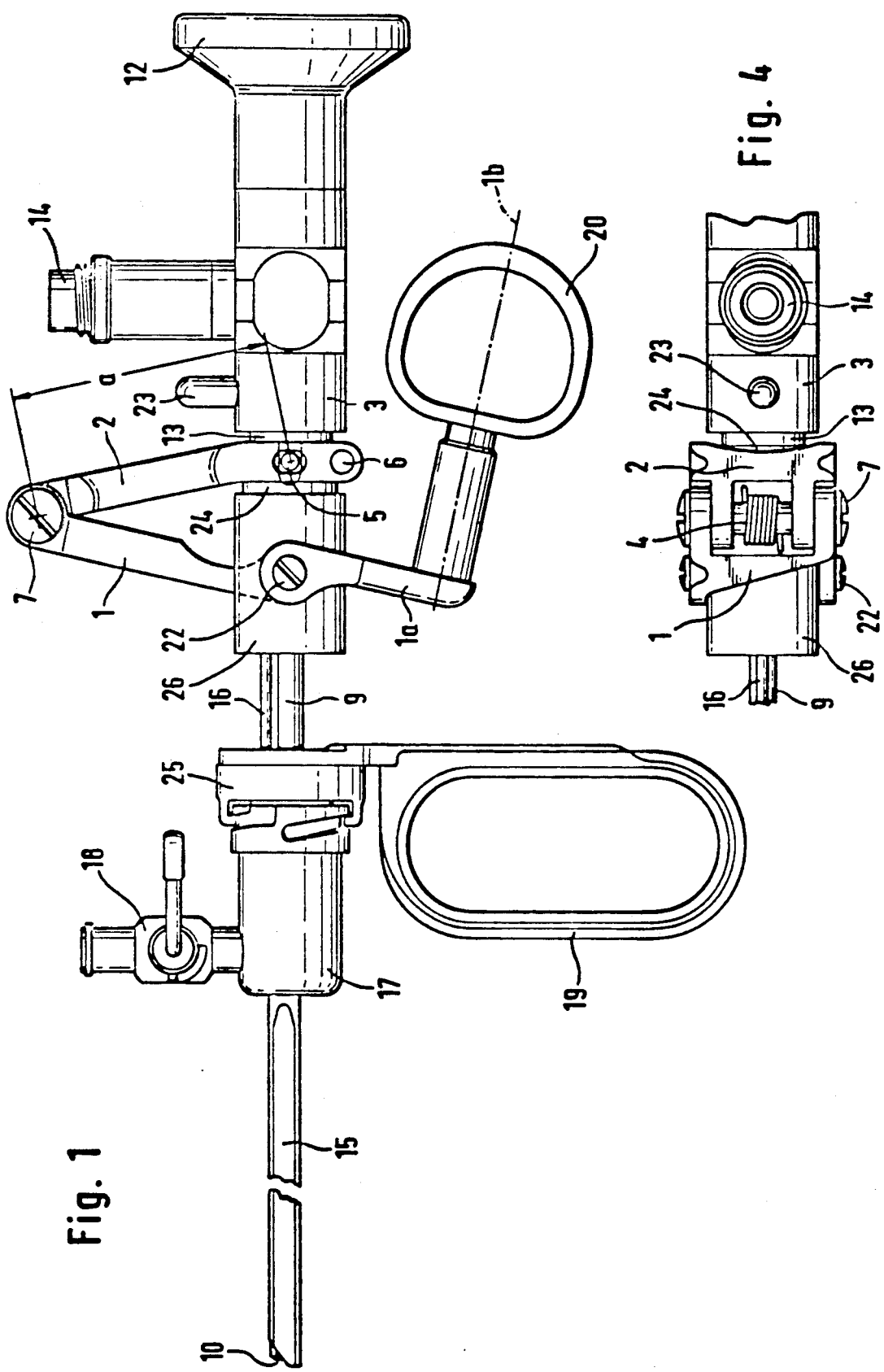
FIG. 1 is a side view of the embodiment.
Figure 2:
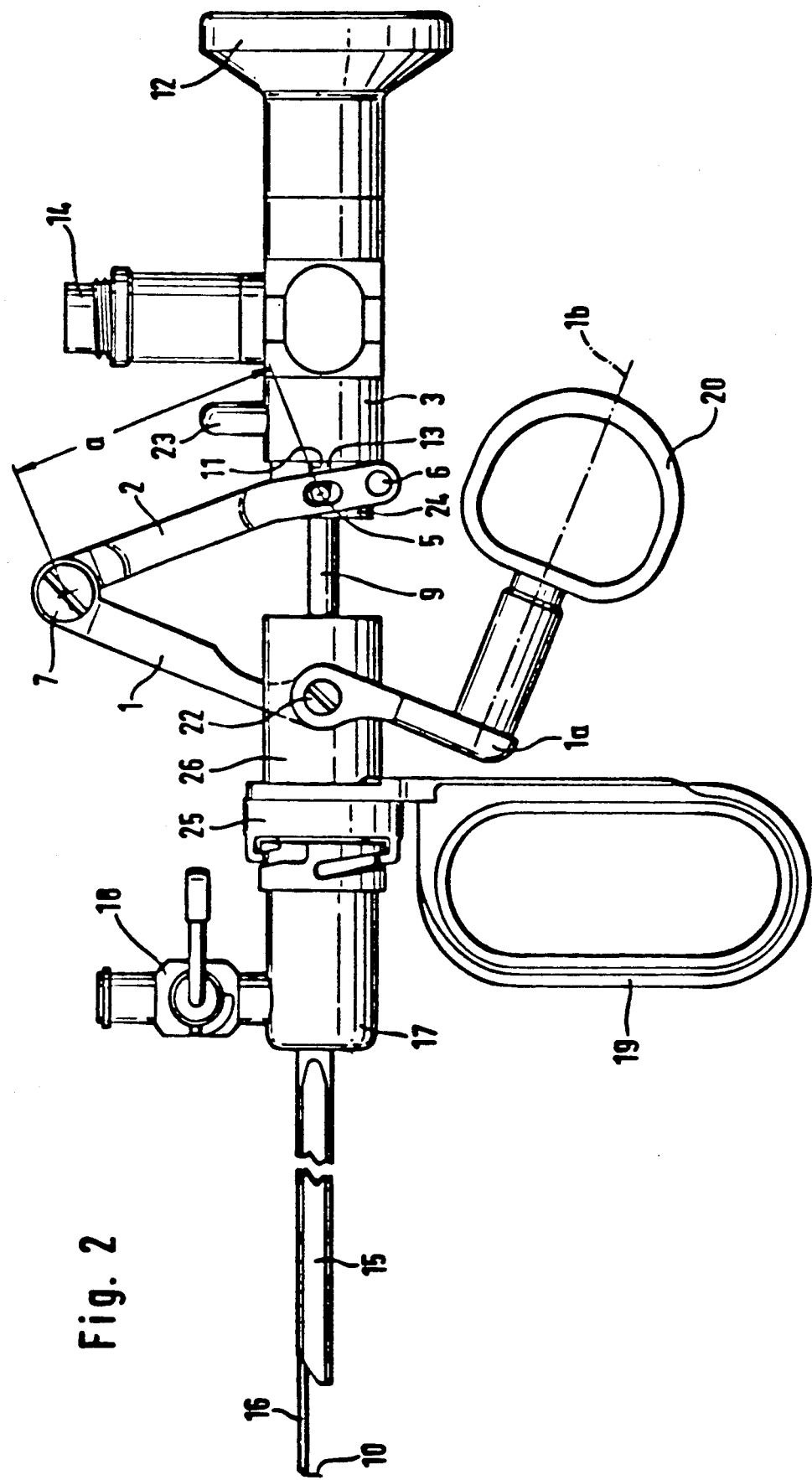
FIG. 2 is a side view as in FIG. 1.

FIG. 1 shows to the left the endoscope shaft 15, in which is arranged the wire loop 10 (not shown in FIG. 1) with the wire loop carrier 16 in the retracted position, (cf. FIG. 2). It is also possible to see in FIG. 3 only the endoscopic periscope 8 located therein. By means of a bayonet catch 25 the head part 17 can be separated together with the endoscope shaft 15 from the fixed handle 19 through which the surgeon can introduce two fingers.

Above this is connected the loop carrier 16 and below it the fixed sleeve 9, to which is fixed the handle 19. The periscope 8, located in a fixed sleeve 9, is mobile, as will be explained hereinafter. Such bayonet catches and rinsing means are well known, therefore no further explanation is required here.

The slide 26 is longitudinally movable on the fixed sleeve 9, the loop carrier 16 being fixed at the top to the slide 26 and is moved together with the latter. For this purpose two levers 1, 2 are provided, which are interconnected by the joint 7. Lever 1 is articulated to the slide 26 by the joint 22. On the opposite side of the endoscope the lever 1a is connected to the lower extension of the lever, which is in turn connected to the thumb ring 20, which is slightly rotatable about its longitudinal axis, namely the longitudinal axis 1b of the lever 1.

The lever 2 is articulated to the lower joint 6, which is fixed to the fixed ring 24. The second joint 5 of the lever is connected by means of a joint pin or bolt 5 to a movable ring 13, which is in turn screwed to the eyepiece 12 by the bayonet catch ring 3, as will be explained relative to FIG. 3.

FIG. 2 shows the above in the operating position, in which the thumb ring 20 has been moved to the left to the patient-near end. Thus, the loop carrier 16 with its wire loop 10 is extended at the patient-near end, in that the slide 26 is moved by the lever 1 to the left to strike against the handle 19. This movement takes place under the action of a spring located in the joint 7 and as will be explained hereinafter relative to FIG. 4.

During the movement to the left of the lever 1, the lever 2 is also moved to the left via the joint 7. This movement takes place about the fixed joint 6, while the joint 5 is moved together with the lever 2 to the left, so that the joint bolt 5 is entrained in the elongated hole 1 of the underlying ring 13 and is firmly connected by the bayonet catch ring 3 to the eyepiece 12, as will be explained relative to FIG. 3.

As now the distance between the joints 5 and 6 is much smaller than the distance a between the joints 5 and 7, there is a limited follow-up of the eyepiece 12 compared with the movement of the slide 26 and therefore the wire loop 10 at the patient-near end.

A portion of the elongated hole 11 is visible in FIG. 2, but it is completely concealed in FIG. 1. The light guide connection 14 and the cock 8 are known components.

Figure 3:
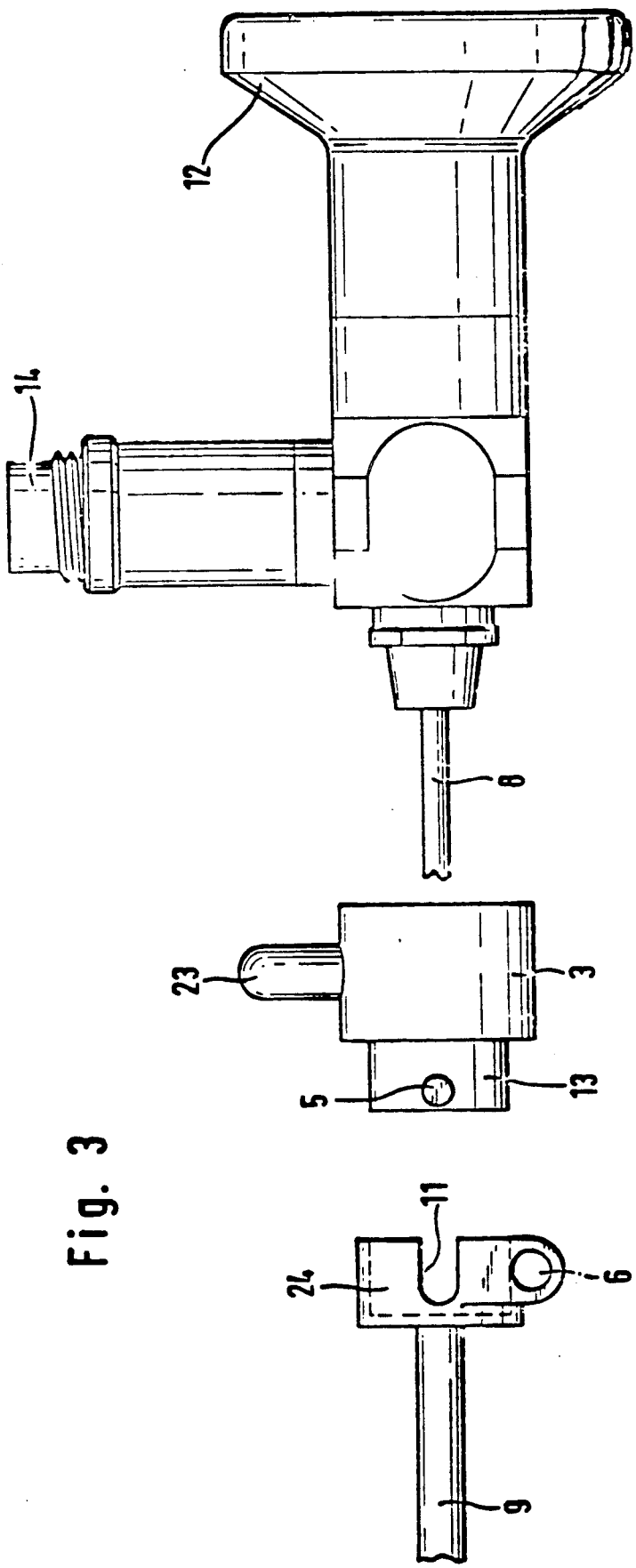
FIG. 3 is a side view of a detail of the disassembled parts on a larger scale.

While omitting the levers 1, 2 and the remaining patient-near endoscope parts, FIG. 3 shows the aforementioned construction in detail, the parts 24, 3 and 12 being reciprocally dismantled and positioned at a distance from one another. To the left it is possible to see the fixed ring 24, which is firmly connected to the fixed sleeve 9 and the joint 6. It is readily possible to see the elongated hole 11 in the central region and the joint pin 5 which fits into fixed ring 24.

Further to the right, the ring 13 is provided with a bayonet ring 3 fixable by the handle 23 to the eyepiece 12 with the light guide connection 14. It is also possible to see the relatively thin periscope 8, which in the fitted state extends up to the patient-near end of the endoscope shaft 15, where the objective of the periscope 8 is located.

For assembly purposes the ring 13 is first inserted into ring 24, so that the joint pin 5 is located in the elongated hole where it can be moved axially with clearance. By operating the handle 23, the eyepiece 12 with the bayonet ring 3 is screwed to the movable ring 13.

FIG. 4 shows a plan view only of the central part of the endoscope. It is in particular possible to see that a spring 4 is arranged around the joint pin 7 which interconnects the two levers 1 and 2 and compresses the latter. This leads to the position according to FIG. 1. The remaining parts have already been referred to hereinbefore and the reference numerals are the same.

The invention more particularly leads to easier handling because the handle 19 can generally be held by two fingers of the surgeon whereas the thumb is guided in the thumb ring 20 which is very comfortable because the thumb ring is rotatable about its axis. Moreover, the greatly simplified lever arrangement leads to an easier action of the sliding link mechanism and, in a desirable manner, the eyepiece is moved much less than the wire loop.

The invention is not restricted to the embodiment described and one skilled in the art can also use the same in other types of medical instruments. In addition, modifications are possible within the scope of the claims.

I claim:

1. A medical instrument with an endoscope in which one of a wire loop, gripper arms or the like is displaceable in the longitudinal direction of the endoscope, comprising:
   (a) one of a wire loop, gripper arms or the like and a carrier therefor, both displaceable in the longitudinal direction of the endoscope,
   (b) a periscope disposed in a fixed sleeve,
   (c) an axially displaceable slide movable on said sleeve,
   (d) first, second, third and fourth joints,
   (e) a fixed ring connected to said sleeve,
   (f) first and second levers interconnected by said first joint, said first lever connected to said axially displaceable slide, said first lever being connected by said second joint to said slide, said second lever being connected by said third joint to said fixed ring,
   (g) a movable ring disposed within said fixed ring and secured to said periscope,
   (h) said fourth joint connected to an end portion of said second lever and said movable ring so that the periscope displacement is smaller than the wire loop electrode displacement.

2. Medical instrument according to claim 1, wherein said joint is positioned on the outer edge of said fixed ring and said fourth joint is positioned substantially in the center of said movable ring.

3. Medical instrument according to claim 1 wherein said fixed ring includes and elongated hole, said fourth joint disposed therein.

4. Medical instrument according to claim 1, further including a restoring spring positioned in said first joint between said first lever and said second lever.

* * * * *